United States Patent
Liu et al.

(10) Patent No.: US 6,833,458 B2
(45) Date of Patent: Dec. 21, 2004

(54) PRACTICAL SYNTHESES OF CHIRAL TRANS-3, 4-DISUBSTITUTED PIPERIDINES AND THE INTERMEDIATES

(75) Inventors: Lee Tai Liu, Taipei (TW); Hsiang-Ling Huang, Taipei (TW); Pao-Chiung Hong, Taipei (TW); Shyh-Fong Chen, Taipei (TW)

(73) Assignee: Development Center for Biotechnology, Taipei (TW)

( * ) Notice: Subject to any disclaimer, the term of this patent is extended or adjusted under 35 U.S.C. 154(b) by 0 days.

(21) Appl. No.: 10/156,499

(22) Filed: May 28, 2002

(65) Prior Publication Data

US 2002/0169323 A1 Nov. 14, 2002

Related U.S. Application Data

(63) Continuation-in-part of application No. 09/587,300, filed on Jun. 5, 2000, now abandoned.

(51) Int. Cl.$^7$ .................... C07D 405/12; A61K 31/445
(52) U.S. Cl. ........................ 546/197; 514/321
(58) Field of Search .......................... 546/197; 514/321

(56) References Cited

U.S. PATENT DOCUMENTS

| | | | |
|---|---|---|---|
| 3,912,743 A | 10/1975 | Christensen et al. | ... 260/293.58 |
| 4,007,196 A | 2/1977 | Christensen et al. | ... 260/293.58 |
| 4,861,893 A | 8/1989 | Borrett | ........................ 546/185 |
| 4,902,801 A | 2/1990 | Faruk et al. | ................ 546/220 |
| 5,258,517 A | 11/1993 | Zepp et al. | ................. 546/240 |

FOREIGN PATENT DOCUMENTS

WO    WO 98/53824    * 12/1998

OTHER PUBLICATIONS

Polniaszek et al. "Stereoselective nuycleophilic additions . . . " J. Org. chem. v. 55, p. 215–223 (1990).*
Yu et al. "Asymmetric synthesis . . . " Tetrahedron Lett. 41, 5647–5641 (2000).*
Yamamoto et al. "Asymmetric synthesis of optically . . . " Ag. biol. chem. v.52, p. 3087–3092 (1988).*
Alan P. Kozikowski et al., *J. Med. Chem.*, 1998, 41:1962–1969.
Mercedes Amat et al., *Tetrahedron: Asymmetry*, 1996, vol. 7, No. 6, 1591–1594.
Klaus Weber et al., *Synlett*, 1998, 885–886.
Beat Wirz et al., *Tetrahedron: Asymmetry*, 1992, vol. 3, No. 8, 1049–1054.
Hans–Josef Altenbach et al., *Tetrahedron: Asymmetry*, 1998, 9:1519–1524.
A.I. Meyers, et al. *Tetrahedron Letters*, 1981, vol. 22, No. 51, 5123–5126.
A.I. Meyers et al., *Heterocycles*, 1982, 18:13–16.
Pierre Mangeney et al.,*J. Org. Chem.*, 1994, 59:1877–1888.
James Cason, *Organic Syntheses Collective*, vol. 4, 1963, p. 630.
Peter D. Theisen et al., *J. Org. Chem.*, 1993, 58:142–146.
L.F. Fieser et al., *Organic Syntheses Collective*, vol. 2, 1943, 560.
Donald S. Karenewsky et al., *J. Org. Chem.*, 1991, 56:3744–3747.
Marc Rodriguez et al., *Tetrahedron Letters*, 1991, vol. 32, No. 7, 923–926.
C. Herdeis et al., *Tetrahedron Asymmetry*, 1996, 7:867–884.
J. Matsuo, *Tetrahedron Letters*, 1996, 39:9723–9726.
K. Akiba, *Tetrahedron Letters*, 1982, 23:429–432.

* cited by examiner

Primary Examiner—Celia Chang
(74) Attorney, Agent, or Firm—Morgan & Finnegan, LLP

(57) ABSTRACT

A new method for the preparation of chiral 4-substituted 2-piperidinones, trans-3,4-disubstituted 2-piperidinones, and trans-3,4-disubstituted piperidines is invented. Chiral paroxetine can be obtained from a chiral trans-3,4-disubstituted piperidine intermediate in high purity and good selectivity.

21 Claims, No Drawings

PRACTICAL SYNTHESES OF CHIRAL TRANS-3, 4-DISUBSTITUTED PIPERIDINES AND THE INTERMEDIATES

This is continuation-in-part of application Ser. No. 09/587,300, filed Jun. 5, 2000, now abandoned.

BACKGROUND OF THE INVENTION

1. Field of the Invention

The present invention relates to a new method for the preparation of chiral trans-3,4-disubstituted piperidines, and particularly to the preparation of chiral paroxetine by using a chiral amine as a chiral auxiliary.

2. Description of the Prior Art

Paroxetine, a type of a trans-3,4-disubstituted piperidine derivative, is a potent selective serotonin (5-hydroxytryptamine) reuptake inhibitor and has been widely used as antidepressant and anti-Parkinson agents.

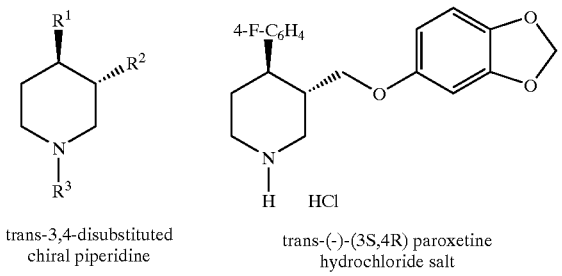

trans-3,4-disubstituted chiral piperidine trans-(-)-(3S,4R) paroxetine hydrochloride salt The trans-(−)-(3S,4R) paroxetine, the pharmacologically active enantiomer, is generally synthesized from the corresponding chiral precursors. Current processes for the production of these chiral precursors involve a selective recrystallization of diastereomeric salts,[1b,e] a biocatalytically kinetic resolution of a racemic ester,[1f] and a chiral auxiliary assisted asymmetric Michael addition.[2] In general, the requirement of a successful resolution of a racemic compound is that its diastereomeric salt must be in the form of good crystals. However, it has been reported that some racemic trans-3,4-piperdine derivatives could not be resolved owing to the non-crystalline salts.[1g] It is also observed that some of the diastereomeric salts of racemic paroxetine and piperidine analogues were not crystalline. Over the past years, although several chiral 3- or 4-substituted piperidine derivatives have been prepared in high enantiomeric purity via chemical or enzymatic method,[2-5] it has been found that the use of chromatography in the purification of non-solid products may retard the application in a large scale process and in industry. The related references are listed at the end of the specification and are incorporated herein for reference in their entirety.

Recently, the asymmetric synthesis of a few specific chiral 3-, 4-substituted, and 3,4-disubstituted 2-piperidinones have been published in the literature.[2-3] However, the general synthetic methods used for the preparation of chiral 3,4-disubstituted 2-piperidinone and piperidine derivatives are still very limited.[2-3] Because chiral 2-piperidinones have been regarded as useful precursors for the synthesis of the corresponding chiral piperidines, the present invention is interested in developing a convenient method for the preparation of these compounds. Herein, the present invention provides a diastereoselective synthesis of a chiral 4-substituted as well as 3,4-disubstituted 2-piperidinones using commercially available chiral amines comprising chiral primary amines or chiral amino acid derivatives, such as (S)-methyl benzylamine as a chiral auxiliary, and the application of this methodology in the preparation of several chiral trans-3,4-disubstituted piperidine derivatives such as paroxetine.

SUMMARY OF THE INVENTION

Accordingly, it is an object of the present invention to provide a new method for the preparation of chiral 4-substituted 2-piperidinones from the corresponding 3-substituted glutaric anhydride and a chiral amine as the intermediates for the synthesis of chiral 3,4-disubstituted 2-piperidinones.

A further object of the present invention is to provide a diastereoselective synthesis of chiral 4-substituted as well as 3,4-disubstituted 2-piperidinones using a commercially available chiral amine as a chiral auxiliary which can be used in a large scale process.

It is still a further object of the present invention is to provide a method for the preparation of trans-3,4-disubstituted piperidines by acylation at the alpha carbon of 4-substituted 2-piperidinones to create trans-3,4-disubstituted 2-piperidinones, followed by reduction Another object of the present invention is to provide a convenient method for the preparation of a chiral paroxetine from a chiral 4-aryl substituted 2-piperidinone via four steps: acylation at the alpha carbon to create a chiral trans-3,4-disubstituted 2-piperidinone, reduction to form a pure trans 3,4-disubstituted piperidine, convertion of the amino alcohol to an aryl ether, and hydrogenolysis of the chiral auxiliary to obtain a chiral paroxetine.

These and other objects, advantages and features of the present invention will be more fully understood and appreciated by reference to the written specification and appended drawings.

DETAILED DESCRIPTION OF THE INVENTION

The present invention relates to a new method for the preparation of a chiral 4-substituted 2-piperidinones from 3-substituted glutaric anhydrides and a chiral amine such as (S)-1-phenylethylamine via four steps. Diastereoselective amidation of the 3-aryl glutaric anhydride with a chiral amine gives chiral hemiamides. Functional group transformations of the amide followed by cyclization provide chiral 4-aryl substituted 2-piperidinones. According to the present invention, a method for t preparation of chiral 4-substituted 2-piperidinones comprises:

(1) reacting a 3-substituted glutaric anhydride of the formula

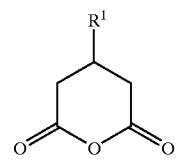

wherein $R^1$ is aryl, alkyl, or any other groups, with a chiral amine of the formula (I)

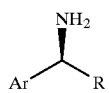

as a chiral auxiliary to obtain a mixture of hemiamides, wherein Ar represents aromatic groups and R represents alkyl groups;
(2) reducing an acid group of the hemiamide to a primary alcohol;
(3) halogenating the primary alcohol to give a halide; and
(4) cyclizing the halide with a base to produce a chiral 2-piperidinone.

The chiral amine used in step (1) of the process of the present invention may be chiral primary amines or chiral amino acid derivatives. Preferably, the aromatic group of the chiral amine is phenyl and the alkyl group of the chiral amine is methyl. More preferably, the chiral auxiliary used in the present invention is 1-phenylethylamine, particularly (S)-1-phenylethylamine. The chiral amine may be added in an amount sufficient to react with the 3-aryl glutaric anhydride, and preferably in a stoichiometric amount. Any conventional reaction conditions can be used in the present invention.

The substituent $R^1$ may be substituted by aryl, alkyl, or any other groups such as alkoxy (OR), amino ($NR_2$), fluoro (F), chloro (Cl), bromo (Br), iodo (I). The substituent $R^1$ is preferably substituted in the 4 position and is $4-F-C_6H_4$.

Halogenating in step (3) of the process of the present invention is preferably bromizating so the product formed in step (3) is bromide.

The chiral 4-substituted 2-piperidinones is the crucial intermediates for the synthesis of a chiral 3,4-disubstituted 2-piperidinones and the corresponding piperidines. After the four steps to prepare chiral 4-substituted 2-piperidinones from 3-substituted glutaric anhydrides and a chiral amine, acylation at the alpha carbon creates chiral trans-3,4-disubstituted 2-piperidinones. After reduction of the lactam, the 2-piperidinones can be smoothly converted to the enantiomerically pure trans- Therefore, the present invention provides a method for the preparation of chiral trans-3,4-disubstituted 2-piperidinones comprising:

(1) reacting a 3-substituted glutaric anhydride of the formula

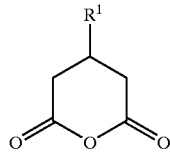

wherein $R^1$ is aryl, alkyl, or any other groups, with a chiral amine of the formula (I)

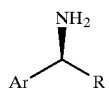

as a chiral auxiliary to obtain a mixture of hemiamides, wherein Ar represents aromatic groups and R represents alkyl groups;

(2) reducing an acid group of the hemiamide to a primary alcohol;
(3) halogenating the primary alcohol to give a halide;
(4) cyclizing the halide with a base to produce a chiral 2-piperidinone; and
(5) acylating an alpha carbon of the 2-piperidinone to give a chiral trans-3,4-disubstituted 2-piperidinone.

Furthermore, it is noteworthy that most of the compounds in the process of the present application are solid and can be easily purified by a simple recrystallization. Besides, all the reagents are nearly nontoxic and environmentally benign.

On another aspect, the present invention provides a method for the preparation of chiral trans-3,4-disubstituted-piperidines of the formula of

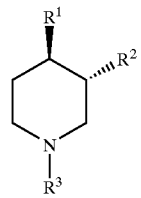

wherein $R^1$ is aryl, alkyl, or any other groups, $R^2$ is alkyl, or any group substituted alkyl, and $R^3$ is hydrogen, alkyl, or any group substituted alkyl, comprising:

(1) reacting a 3-substituted glutaric anhydride of the formula

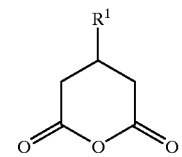

wherein $R^1$ is aryl, alkyl, or any other groups, with a chiral amine of the formula (I)

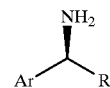

as a chiral auxiliary to obtain a mixture of hemiamides, wherein Ar represents aromatic groups and R represents alkyl groups;
(2) reducing an acid group of the hemiamide to a primary alcohol;
(3) halogenating the primary alcohol to give a halide;
(4) cyclizing the halide with a base to produce a chiral 2-piperidinone;
(5) acylating at the alpha carbon of the 2-piperidinone to give a chiral trans-3,4-disubstituted 2-piperidinone; and
(6) reducing ester and amide groups of the chiral trans-3,4-disubstituted 2-piperidinone to form a trans-3,4-disubstituted piperidine.

The present invention also provides a method for the preparation of a chiral paroxetine comprising:

(1) reacting a 3-aryl glutaric anhydride of the formula

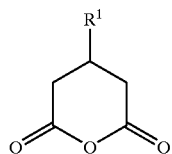

wherein $R^1$ is aryl, with a chiral amine of the formula (I)

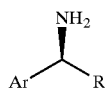

as a chiral auxiliary to obtain a mixture of hemiamides, wherein Ar represents aromatic groups and R represents alkyl groups;
(2) reducing an acid group of the hemiamide to a primary alcohol;
(3) halogenating the primary alcohol to give a halide;
(4) cyclizing the halide with a base to produce a chiral 2-piperidinone;
(5) acylating at the alpha carbon of the 2-piperidinone to give a chiral trans-3,4-disubstituted 2-piperidinone;
(6) reducing ester and amide groups of the chiral trans-3,4-disubstituted 2-piperidinone to provide a trans-3,4-disubstituted piperidine; and,
(7) converting a hydroxyl group of trans-3,4-disubstituted piperidine to an aryl ether and then removing the chiral auxiliary by hydrofenolysis to obtain a chiral paroxetine hydrochloride.

The above step (7) of the inventive method for the preparation of a chiral paroxetine can be substituted by the following three steps:

(7) crystallizing the trans-3,4-disubstituted piperidine and converting a hydroxyl group of this compound to a sulfonate followed by a treatment with sesamol and potassium alkoxide to provide a free amine;
(8) converting the free amine to a hydrochloride salt and purifying the hydrochloride salt by recrystallization; and
(9) removing the chiral auxiliary by hydrogenolysis to obtain a chiral paroxetine hydrochloride.

As stated above, the chiral amine used in step (1) of the present invention may be chiral primary amines or chiral amino acid derivatives.
The chiral amine may be added in an amount sufficient to react with the 3-aryl glutaric anhydride, and preferably in a stoichiometric amount.

In accordance with the present invention, the synthetic procedures of a preferred embodiment of the process are described in the following Scheme 1. The required starting material, 3-aryl-glutaric anhydride 6, was prepared from the commercially available 4-fluorophenyl cinnamic acid 1 via four steps. The acid 1 was first converted to the corresponding methyl ester 2, which then underwent Michael addition with dimethyl malonate in sodium/methanol solution to form a triester 3.[6] After hydrolysis, decarboxylation,[7] and dehydration,[8] a prochiral 3-fluorophenyl glutaric anhydride 6 was obtained in the form of white needle crystals.

Desymmetryzation of meso anhydride 6 with (S)-methyl benzylamine in toluene at −78° C. provided a mixture of hemiamides 7a and 7b, wherein $R^1$ represents 4-F—$C_6H_4$ and $R^2$ represents H in hemiamide 7a, and $R^1$ represents H and $R^2$ represents 4-F—$C_6H_4$ in hemiamide 7b, and hemiamide 7a was assigned as the major product according to literature.[9] The hemiamides 7a and 7b are novel. Proton NMR spectrum of the crude product showed that the ratio of the two diastereomers 7a and 7b was about 4.5–5.5:1 (60–70% de). The abbreviation "de" means the purity of a major product ($D_1$) in two diastereomers ($D_1$ and $D_2$), and is calculated by the following equation:

$$de = (D_1 - D_2)/(D_1 + D_2) \times 100\%$$

One recrystallization of the crude product enhanced the diastereomeric purity of the major hemiamide 7a to 90–95% de in a 70% yield. The second and the third crops containing mixtures of diastereomers 7b and 7a were hydrolyzed with concentrated hydrochloric acid to recover diacid 5. The acid group of hemiamide 7a was converted to a primary alcohol of compound 8 via a reduction of the corresponding mixed anhydride with sodium borohydride.[10] The primary alcohol compound 8 with the substituent X being hydroxy (OH) is novel. Bromonation of alcohol 8 with phosphorous bromide and hydrobromic acid gave a new bromide 9, wherein X represents Br. Treatment of bromide 9 with sodium hydride in a refluxed tetrahydrofuran suspension formed a new chiral 2-piperidinone 10. Proton NMR spectrum showed that 2-piperidinone 10 was a pure diastereomer (>99% de) without any existence of the other diastereomer.

Acylation at the alpha carbon of 2-piperidinone 10 by treatment with excess amount of base, such as lithium diisopropyl amide (LDA), lithium hexamethyldisilane (LiHMDS) and sodium hydride (NaH) and methyl chloroformate in a solvent such as tetrahydrofuran (THF) and diethyl ether gave a novel ester 11 in satisfactorily yield and diastereoselectivity. Proton NMR spectrum showed that only one compound was obtained, which was assigned as the trans stereoisomer. The single crystal X-ray analysis of the new compound 11 confirms the (4S, 3R) absolute configuration, and therefore, the stereochemistry of acid 7a. Reduction of the ester and the amide groups of 2-piperidinone 11 with lithium aluminum hydride provided a novel amino alcohol 12, wherein R represents hydrogen. Compound 11 was viscous oil and was very slowly solidified on standing. However, compound 12 was easy to crystallize after column chromatography. Conversion of the hydroxyl group in compound 12 to a new methanesulfonate 13 followed by treatment with sesamol and potassium alkoxide provided a new free amine 14a. Purification of the new free amine 14a can be achieved by conversion of 14a to a new hydrochloride salt 14b. Hydrogenolysis of the benzyl group in 14b formed paroxetine hydrochloride 15 as a viscous mass, which was purified by recrystallization according the literature procedure.[1c]

Scheme 1

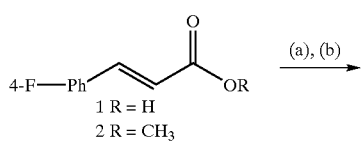

1 R = H
2 R = $CH_3$

-continued

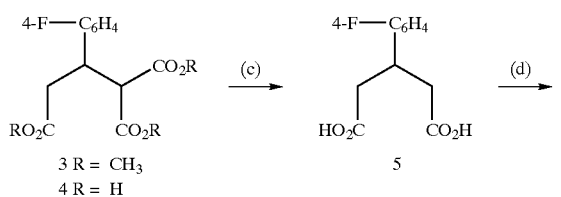

3 R = CH₃
4 R = H

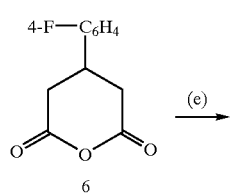

6

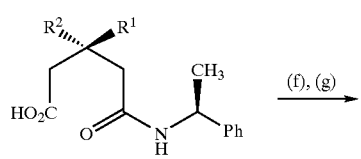

| | R¹ | R² | | R¹ | R² | |
|---|---|---|---|---|---|---|
| 7a | 4-F—C₆H₄ | H | 7b | H | 4-F—C₆H₄ | 8 X = OH |
| 7c | C₆H₅ | H | 7d | H | C₆H₅ | 9 X = Br |
| 7e | CH₃ | H | 7f | H | CH₃ | |

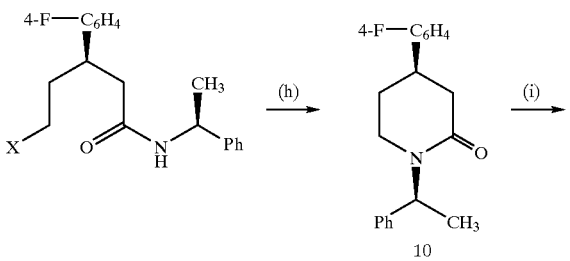

10

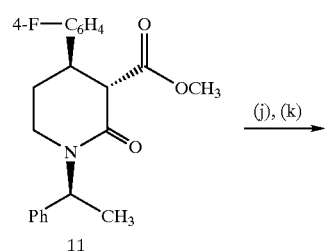

11

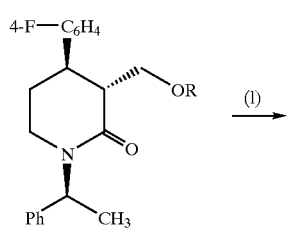

12 R = H
13 R = O₂SCH₃

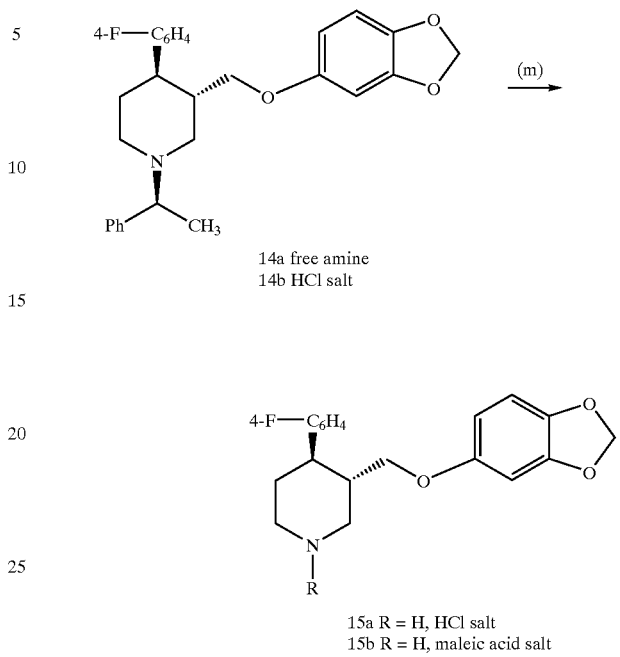

14a free amine
14b HCl salt

15a R = H, HCl salt
15b R = H, maleic acid salt

Please note that the intermediate compounds 7a, 7b, 8, 9, 10, 11, 12, 13, 14a and 14b in Scheme 1 are novel. Any suitable reagents and reaction conditions can be used in the process of the present invention. The reagents and conditions used in each step as shown in Scheme 1 are the preferred embodiment, and for example, are: (a) sodium methoxide, dimethyl malonate, methanol, refluxed for 20 hours, 70% yield; (b) 1 N sodium hydroxide, refluxed for 20 hours; (c) concentrated hydrochloric acid, refluxed for 20 hours, 70% steps (two steps); (d) acetyl chloride, refluxed for 20 hours, 90% yield; (e) (S)-methylbenzylamine, triethylamine, toluene, −78° C., 10 hours, then room temperature 10 hours, 70% yield; (f) triethylamine, iso-butyl chloroformate, tetrahydrofuran, −78–0° C., 20 hours; then, sodium borohydride, water, 0–25° C., 20 hours, 80% yield; (g) phosphorous tribromide, concentrated hydrobromic acid, 0–25° C., 4 days, 70% yield; (h) sodium hydride, tetrahydrofuran, refluxed for 20 hours, 85% yield; (i) lithium diisopropylamide, methyl chloroformate, tetrahydrofuran, −78° C., 10 hours, 78% yield; (j) lithium aluminum hydride, tetrahydrofuran, refluxed, 72 hours, 62% yield; (k) methanesulfonyl chloride, dichloromethane, room temperature, 20 hours; (l) (i) sesamol, sodium, propanol, refluxed for 36 hours; (ii) hydrochloric acid, 65% yield; (m) H₂, 5% Pd—C, methanol, 96% yield.

The following examples are offered by way of illustration. The examples are not intended to limit the scope of the invention in any respect and should not be so construed.

EXAMPLES

Example 1

(3S)-3-(4-Fluorophenyl)-5-oxo-5-(1S)-(1-phenylethylamino)pentanoic Acid (7a)

5.0 g of anhydride 6 in 100 mL of toluene was added dropwise to a solution of 5.25 mL of (S)-methylbenzylamine in 200 mL of toluene at −78° C. After completion of addition, 3.5 mL triethylamine was added dropwise. The mixture was stirred from this temperature to room temperature overnight. After evaporation of toluene, the mixture was stirred with 50 mL of 1 N hydrochloric acid, and then was extracted with hot ethyl acetate. The organic layer was combined, washed with brine, dried over magnesium sulfate, and evaporated to dryness. The crude product was recrystallized to furnish the title compound as a colorless solid in the first crop (70% yield, 90–95% de): mp 195.0–195.5° C.; $[\alpha]^{25}{}_D$=−78.8 (c 1.0, $CH_3OH$); $^1H$ NMR (200 MHz, $CDCl_3$) δ 7.30–7.00 (m, 7 H), 6.95 (t, J=8.7 Hz, 2 H), 5.60 (m, 1 H), 4.94 (quint, J=6.9 Hz, 1 H), 3.58 (m, 1 H), 2.75–2.25 (m, 4 H), 1.26 (d, J=6.9 Hz, 3 H); $^{13}C$ NMR (125 MHz, $CDCl_3/CD_3OD$) δ 176.8, 173.6, 164.3, 145.8, 140.8, 131.6, 131.0, 129.7, 128.6, 117.8, 51.1, 45.3, 43.0, 41.1, 23.9. Anal. Calcd for $C_{19}H_{20}FNO_3$: C, 69.29; H, 6.12; N, 4.25. Found: C, 69.07; H, 6.09; N, 3.83. The mother liquor was concentrated and the solid was recrystallized from ethyl acetate and hexanes to give the second crop, which contained 7a and 7b as a mixture and was hydrolyzed in concentrated acid to recover diacid 5.

Example 2

(3R)-3-(4-Fluorophenyl)-5-hydroxypentanoic Acid (1S)-1-Phenylethylamide (8)

3 mL of triethylamine was added to a solution of 5 g of compound 7a in 200 mL of tetrahydrofuran at room temperature. The solution was stirred for 60 min at room temperature and then was moved to a −78° C. dry ice acetone bath. To this solution was added dropwise 2.6 mL of iso-butyl chloroformate. The suspension was stirred from −78° C. to room temperature overnight. The mixture was filtered through a celite and silica gel pad, and washed with small amount tetrahydrofuran. To this solution in an ice bath was added 2.0 g of sodium borohydride, followed by dropwise addition of 10 mL of water. Carbon dioxide gas evolved violently. The reaction mixture was stirred for 2–4 hr, and was filtered through a celite pad. After the solvent evaporated, the aqueous layer was extracted several times with ethyl acetate. The organic layer was combined, washed with brine, dried over magnesium sulfate, and concentrated. The solid was recrystallized from ethyl acetate and hexanes to form the title compound as a colorless solid (80% yield, 95% de): mp 170.0–170.5° C.; $[\alpha]^{25}{}_D$=−86.4 (c 1.0, $CH_3OH$); $^1H$ NMR (200 MHz, $CDCl_3$) δ 7.40–7.10 (m, 7 H), 6.98 (t, J=8.7Hz, 2 H), 5.51 (br d, J=7.7 Hz, 1 H), 5.00 (quint, J=7.4 Hz, 1 H), 3.60–3.50 (m, 2 H), 3.33 (m, 1 H), 2.55 (dd, J=6.6, 14.2 Hz, 1 H), 2.38 (dd, J=8.6, 14.2 Hz, 1 H), 1.95–1.75 (m, 2 H), 1.27 (d, J=6.9 Hz, 3 H); $^{13}C$ NMR (125 MHz, $CDCl_3$) δ 170.6, 161.6, 142.9, 139.6, 128.9, 128.6, 127.4, 126.1, 115.4, 60.1, 48.6, 44.0, 38.9, 38.4, 21.3. Anal. Calcd for $C_{19}H_{22}FNO_2$: C, 72.36; H, 7.03; N, 4.44. Found: C, 72.35; H, 6.83; N, 4.33.

Example 3

(3S)-5-Bromo-3-(4-fluorophenyl)pentanoic Acid (1S)-1-Phenylethyl Amide (9)

To a solution of 4.5 g of alcohol 8 250 mL of dry ethyl ether in an ice bath was added dropwise of 1.7 mL of phosphorous tribromide. After stirring for 3 days in an ice bath, 0.5 mL of conc. hydrobromic acid was added to this mixture. The resulting solution was stirred continuously at room temperature overnight, and 100 mL of ice was added to quench the reaction. The white solid was collected, dissolved in ethyl acetate, washed with saturated sodium hydrocarbonate solution and saturated brine. The organic layer was filtered through a silica gel pad. After the solvent evaporated, the crude solid was recrystallized from ethyl acetate and hexanes to form 3.8 g of the title compound as a white solid (72% yield, >95% de): mp 156.5–157.5 ° C.; $[\alpha]^{25}{}_D$=−38.2 (c 1.0, $CH_3OH$); $^1H$ NMR (200 MHz, $CDCl_3$) δ 7.40–7.10 (m, 7 H), 6.99 (m, 2 H), 5.52 (br d, J=7.6 Hz, 1 H), 4.98 (m, 1 H), 3.35–3.20 (m, 2 H), 3.05 (m, 1 H), 2.51 (dd, J=6.3, 14.0 Hz, 1 H), 2.37 (dd, J=8.7, 14.0 Hz, 1 H), 2.25–2.05 (m, 2 H), 1.25 (d, J=6.9 Hz, 3 H); $^{13}C$ NMR (125 MHz, $CDCl_3$) δ 169.7, 161.8, 142.8, 137.7, 129.1, 128.6, 127.4, 126.1, 115.7, 48.6, 44.0, 40.6, 38.7, 30.9, 21.3. Anal. Calcd for $C_{19}H_{21}BrFNO$: C, 60.33; H, 5.60; N, 3.70. Found: C, 60.57; H, 5.54; N, 3.82.

Example 4

(4R)-[4-(4-Fluorophenyl)-1-(1S)-(1-phenylethyl)]piperidin-2-one (10)

A suspension of 0.7 g of sodium hydride (80% dispersion) in 10 mL of dry tetrahedron was added to a solution of 3.5 g of compound 9 in 40 mL of dry tetrahedron at room temperature. The mixture was heated at 65–75° C. overnight. After cooling to room temperature, the reaction mixture was slowly quenched in an ice bath with 10 mL of methanol. After evaporation of all solvents, the residue was diluted with ethyl acetate and then washed with brine. The organic layer was collected and filtered through a silica gel pad. After removal of solvent, the crude solid was recrystallized from ethyl acetate and hexanes to form 2-piperidinone 10 as colorless crystals (87% yield, >99% de): mp 163.5–164.0° C.; $[\alpha]^{25}{}_D$=−108.4 (c 1.0, $CHCl_3$); $^1H$ NMR (200 MHz, $CDCl_3$) δ 7.36–7.25 (m, 5 H), 7.13 (m, 2 H), 7.00 (m, 2 H), 6.18 (q, J=7.08 Hz, 1 H), 3.16–2.87 (m, 2 H), 2.87–2.69 (m, 2 H), 2.55 (dd, J=10.1, 17.4 Hz, 1 H), 2.05–1.78 (m, 2 H), 1.51 (d, J=7.1 Hz, 3 H); $^{13}C$ NMR (125 MHz, $CDCl_3$) δ 168.7, 161.6, 140.0, 139.3, 128.5, 128.0, 127.6, 127.4, 115.5, 49.8, 40.3, 39.6, 37.5, 30.3, 15.1. Anal. Calcd for $C_{19}H_{20}FNO$: C, 76.74; H, 6.78; N, 4.71. Found: C, 76.93; H, 6.82; N, 4.30.

Example 5

(3S,4R)-[4-(4-Fluorophenyl)-3-methoxycarbonyl-1-(1S)-(1-phenylethyl)]piperidin-2-one (11a)

19.5 mL of 1.5 M solution of lithium disiopropylamide in cyclohexane was added dropwise to a stirred solution of 2 g of lactam 10 in 50 mL of tetrahydrofuran at −78° C. After 1 hour, 0.8 mL of methyl chloroformate was added dropwise. The resultant solution was stirred for 4 hr at −78° C., and then was quenched at this temperature with aqueous solution of ammonium chloride. The mixture was concentrated to evaporate tetrahydrofuran, and the water layer was extracted with ethyl acetate. The combined organic layer was washed with brine, dried over magnesium sulfate, filtered, and concentrated to form a yellow viscous oil which was very slowly solidified on standing. Recrystallization from ethyl acetate and hexanes gave 1.85 g (78%) of the title compound as white needle crystals: mp 73.5–74.5° C.; $[\alpha]^{25}{}_D$=−181.2 (c 1.0, $CHCl_3$); $^1H$ NMR (500 Mz, $CDCl_3$) δ 7.45–7.30 (m, 5 H), 7.20–7.16 (m, 2 H), 7.06–7.00 (m, 2 H), 6.17 (q, J=7.03 Hz, 1 H), 3.70 (s, 3 H), 3.64 (d, J=10.2 Hz, 3 H), 3.39 (td, J=3.5, 10.7 Hz, 1 H), 3.17 (dt, J=4.9, 12.6 Hz, 1 H), 2.88 (m, 1 H), 2.05 (m, 1 H), 1.96 (m, 1 H), 1.57 (d, J=7.0 Hz, 3 H); $^{13}C$ NMR (125 MHz, $CDCl_3$) δ 170.6, 165.4, 161.9, 139.4, 137.4, 128.6, 128.3, 127.5, 115.7, 56.6, 52.3, 50.4, 41.4, 40.5, 29.4, 15.0. Anal. Calcd for $C_{21}H_{24}FNO_3$: C, 70.57; H, 6.77; N, 3.92. Found: C, 70.97; H, 6.17; N, 4.01.

Example 6

(3S,4R)-[4-(4-Fluorophenyl)-3-hydroxymethyl-1-(1S)-(1-phenylethyl)]piperidine (12)

5.6 g of ester 11 was added dropwise to a suspension of 6 g of lithium aluminum hydride in 150 mL of tetrahydrofuran under nitrogen atmosphere. The mixture was refluxed for three days and then was treated with 10 mL of water, 6 mL of 15% sodium hydroxide solution, and 25 mL of water in an ice bath. After filtration of precipitates, the organic solution was washed with brine, dried over magnesium sulfate, filtered, and concentrated in vacuo to form 3.2 g (62%) of the crude product as pale yellow solid. Recrystallization from ethyl acetate and hexane gave the title compound as white sheets: mp 130.0–131.0° C.; $[\alpha]^{25}{}_D$=−17.4 (c 1.0, CHCl$_3$); $^1$H NMR (200 MHz, CDCl$_3$) δ 7.40–7.10 (m, 7 H), 7.05–6.90 (m, 2 H), 3.51 (q, J=6.78 Hz, 1 H), 3.45–3.34 (m, 2 H), 3.23 (m, 1 H), 2.89 (m, 1 H), 2.20 (m, 1 H), 2.05–1.80 (m, 4 H), 1.80–1.65 (m, 2 H), 1.44 (d, J=6.8 Hz, 3 H); $^{13}$C NMR (125 MHz, CDCl$_3$) δ 161.4, 143.2, 140.3, 128.8, 128.2, 127.8, 127.0, 115.3, 65.1, 63.9, 54.7, 50.6, 44.4, 34.6, 19.6. Anal. Calcd for $C_{20}H_{24}FNO$: C, 76.65; H, 7.72; N, 4.47. Found: C, 76.86; H, 7.77; N, 4.58.

Example 7

(3S,4R)-[3-(Benzo [1,3]dioxol-5-yloxymethyl)-4-(4-fluorophenyl)-1-(1S)-(1phenylethyl)]-piperidine Hydrochloride Salt (14b)

1.65 mL of triethylamine and 0.86 mL of methanesulfonyl chloride was added dropwise to a solution of 2 g of alcohol 12 in 60 mL of dichloromethane in an ice bath. The mixture was stirred at this temperature for 3 h and was quenched with 30 mL of saturated sodium hydrocarbonate. The aqueous solution was extracted with dichlomethane. The combined organic layer was washed with brine, dried over magnesium sulfate, and concentrated to furnish the mesylate 13 as a yellow viscous oil.

A solution of 3 g of sesamol in 30 mL of propanol was added to a solution of 0.28 g of sodium in 20 mL of propanol. After gently refluxing for 30 min, a solution of mesylate 13 in 50 mL of propanol was added. The mixture was refluxed for 1.5 days, cooled to room temperature, and then quenched with 30 mL of ice water. After evaporation of propanol, the aqueous solution was extracted with ethyl ether. The combined organic layer was washed with 1 N sodium hydroxide solution, brine, dried over magnesium, filtered, and the was concentrated to form the free amine 14a as a red brown viscous oil. The free amine was diluted with 50 mL of methanol, and treated with 0.5 mL of concentrated hydrochloric acid. The resultant solution was stood for several days and yellow solids precipitated. The solids were collected, recrystallized from methanol and ethyl acetate to form 1.92 g of the hydrochloride salt as white needles. mp >250° C. (decomposed); $[\alpha]^{25}{}_D$=−87.4 (c 1.0, CH$_3$OH); $^1$H NMR (500 MHz, CDCl$_3$) δ 7.65–7.60 (m, 2 H), 7.55–7.45 (m, 3 H), 7.30–7.20 (m, 2 H), 6.97 (t, J=8.7 Hz, 2 H), 6.66 (d, J=8.5 Hz, 1 Hz)6.34 (d, J=2.5 Hz, 1 Hz), 6.14 (dd, J=2.5, 8.5 Hz, 1 H), 5.92 (s, 2 H), 4.23 (quintet, J=6.0 Hz, 1 H), 3.86 (m, 1 H), 3.64 (dd, J=2.3, 9.6 Hz, 1 H), 3.49 (dd, J=3.9, 9.6 Hz, 1 H), 3.32 (m, 1 H), 2.9–2.8 (m, 3 H), 2.57 (m, 1 H), 2.02 (d, J=6.9 Hz, 3 H), 1.9 (m, 1 H); $^{13}$C NMR (125 MHz, CDCl$_3$) δ 161.8, 153.7, 148.2, 142.0, 136.9, 133.9, 123.0, 129.4, 129.2, 115.7, 107.9, 105.5, 101.2, 97.9, 67.6, 67.5, 54.6, 49.5, 41.2, 39.3, 29.9, 17.5. Anal. Calcd for $C_{27}H_{29}ClFNO_3$: C, 69.00; H, 6.22; N, 2.98. Found: C, 69.36; H, 6.22; N, 3.07.

Example 8

Paroxetine Hydrochloride or (3S,4R)-[3-(Benzo[1,3]dioxol-5-yloxymethyl)-4-(4-fluorophenyl)] piperidine Hydrochloride (15)

The suspension of 1.6 g of compound 14b and 20 mg of 10% Pd—C in 140 mL of anhydrous methanol was stirred at room temperature under 1 atm of hydrogen gas for 48 h. The resulting suspension was filtered through Celite, washed with methanol, and concentrated in vacuo. The crude paroxetine hydrochloride was obtained as a red viscous mass. Purification was accomplished by recrystallization from methanol-ethyl ether-hexanes to form 0.85 g (68%) of paroxetine hydrochloride as a pink crystals: mp 123–124° C. (Lit.[1c] 129–131° C.); $[\alpha]^{25}{}_D$=−88.6 (c 1.0, CH$_3$OH); $^1$H NMR (500 MHz, CDCl$_3$) δ 7.35–7.25 (m, 2 H), 7.05 (t, J=8.5 Hz, 2 H), 6.68 (d, J=8.4 Hz, 1 H), 6.40 (d, J=2.3 Hz, 1 H), 6.18 (dd, J=2.3, 8.5 Hz, 1 Hz), 5.95 (s, 2 H), 3.83 (d, J=10.3 Hz, 1 H), 3.75 (d, J=12.4 Hz, 1 H), 3.68 (d, J=9.5 Hz, 1 H), 3.24 (m, 1 H), 3.12 (m, 1 H), 2.97 (td, J=3.3, 12.9 Hz, 1 H), 2.75 (m, 1 H), 2.50 (m, 1 H), 2.01 (d, J=13.1 Hz, 1 H); $^{13}$C NMR (125 MHz, CDCl$_3$) δ 161.9, 153.7, 148.2, 142.0, 137.1, 128.9, 115.8, 107.9, 105.6, 101.2, 97.9, 67.5, 46.8, 44.5, 41.7, 39.4, 30.1.

Example 9

(3S,1S')-3-Methyl-5-oxo-5-(1'-phenylethyl-amino)-pentanoic acid

The procedure of Example 1 was followed for the synthesis of the chiral 4-methyl substituted 2-piperidinone identified above. The final product, a colorless solid with $R^1$ being methyl was analyzed by NMR. The yield was 76%, purity was 99% d.e., the m.p. was 118.6–118.8° C.; with $[\alpha]^{25}{}_D$=−88.8 (c 1.0, CH$_3$OH); $^1$H NMR (500 MHz, CDCl$_3$) δ 7.40–7.26 (m, 5 H), 6.03 (d, J=7.4 Hz, 1 H), 5.16 (quint, J=7.3 Hz, 1 H), 2.50–2.38 (m, 2 H), 2.35 (dd, J=6.2, 14.2, Hz, 1H) 2.31 (dd, J=6.6, 14.2 Hz, 1H) 2.23 (dd, J=6.7, 13.9 Hz, 1H) 1.52 (d, J=6.9 Hz, 3H); 1.07 (d, J=6.6 Hz, 3H) $^{13}$C NMR (125 MHz, CDCl$_3$/CD$_3$OD) δ 175.2, 171.9, 148.3, 128.4, 127.1, 125.9, 48.6, 42.6, 40.6, 28.2, 21.7, 19.4. Anal. Calcd for $C_{14}H_{19}NO_3$: C, 67.45; H, 7.68; N, 5.62. Found: C, 67.59; H, 7.66; N, 5.49.

While the invention has been described with respect to certain preferred exemplifications and embodiments, it is not intended to limit the scope of the invention therein, but solely by the claims appended hereto.

References and Notes 1 (a) Christensen, J. A.; Squires, R. F. U.S. Pat. No. 3,912,743, 1975. (b) Christensen, J. A.; Squires, R. F. U.S. Pat. No. 4,007,196, 1977. (c) Barnes, R. D.; Wood-Kaczmar, M. W.; Richardson, J. E.; Lynch, I. R.; Buxton, P. C.; Curzons, A. D. European Patent 0223403, 1987. (d) Borrett, G. T. U.S. Pat. No. 4,861,893, 1989. (e) Faruk, E. A.; Martin, R. T. U.S. Pat. No. 4,902,801, 1990. (f) Zepp, C. M.; Gao, Y.; Heefner, D. L. U.S. Pat. No. 5,258,517, 1993. (g) Kozikowski, A. P.; Araldi, G. L.; Boja, J.; Meil, W. M.; Johnson, K. M.; Flippen-Anderson, J. L.; George, C.; Saiah, E. J. Med. Chem. 1998, 41, 1962.

2 Amat M.; Hidalgo, J.; Bosch, J. *Tetrahedron: Asymmetry* 1996, 7, 1591.
3 (a) Herdeis, C.; Kaschinski, C.; Karla, R., Lotter, H. *Tetrahedron: Asymmetry* 1996, 7, 867. (b) Weber, K.; Gmeiner, P. *Synlett* 1998, 885. (c) Matsuo, J., Kobayashi, S.; Koga, K. *Tetrahedron Lett.* 1996, 7, 9723.
4 (a) Wirz, B.; Walther, *Tetrahedron: Asymmetry* 1992, 3, 1049. (b) Altenbach, H.-J.; Blanda, G. *Tetrahedron: Asymmetry* 1998, 9, 1519.
5 (a) Meyers, A. I.; Natale, N. R.; Aettlaufer, D. G.; Rafii, S.; Clardy, J. *Tetrahedron Lett.* 1981, 22, 5123. (b) Meyers, A. I.; Natale, N. R. *Heterocycles* 1982, 18, 13. (c) Akiba, K.; Iseki, Y.; Wada, M. *Tetrahedron Lett.* 1982, 23, 429. (d) Mangeney, P.; Gosmini, R.; Raussou, S.; Commercon, M.; Alexakis, A. *J. Org. Chem.* 1994, 59, 1877.
6 Cason, J. *Organic Syntheses Collective Vol.* 4, 1963, 630.
7 Theisen, P. D.; Heathcock, C. H. *J. Org. Chem.* 1993, 58, 142.
8 Fieser, L. F.; Martin, E. L. *Organic Syntheses Collective Vol.* 2, 1943, 560.
9 Karanewsky, D.; Malley, M.; Gougoutas, J. Z. *J. Org. Chem.* 1991, 56, 3744.
10 Rodriguez, M.; Llinares, M.; Doulut, S.; Heitz, A.; Martinez, J. *Tetrahedron Lett.* 1991, 32, 923.

We claim:
1. A method for the preparation of a chiral 4-substituted 2-piperidinone comprising:
(1) reacting a 3-substituted glutaric anhydride of the formula

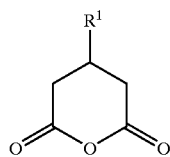

wherein $R^1$ is aryl, or 4-fluorophenyl with chiral amine of the formula (I)

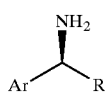

as a chiral auxiliary to obtain a mixture of hemiamides, wherein Ar represents an aromatic groups and R represents an alkyl groups;
(2) reducing an acid group of the hemiamide to a primary alcohol;
(3) halogenating the primary alcohol to give a halide; and
(4) cyclizing the halide with sodium hydride to produce a chiral 2-piperidinone.

2. A method according to claim 1, wherein the chiral amine is chiral primary amines or chiral amino acid derivatives.
3. A method according to claim 1, wherein the aromatic group of the chiral amine is phenyl.
4. A method according to claim 1, wherein the alkyl group of the chiral amine is methyl.
5. A method according to claim 1, wherein the chiral amine is methyl benzylamine.
6. A method according to claim 1, wherein the chiral amine is (S)-methylbenzylamine.
7. A method according to claim 1, wherein $R^1$ is 4-F-$C_6H_4$.
8. A method for the preparation of a chiral trans-3,4-disubstituted 2-piperidinone comprising:

(1) reacting a 3-substituted glutaric anhydride of the formula

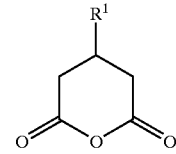

wherein $R^1$ is aryl, or 4-fluorophenyl with a chiral amine of the formula (I)

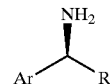

as a chiral auxiliary to obtain a mixture of hemiamides, wherein Ar represents an aromatic group and R represents an alkyl group;
(2) reducing an acid group of the hemiamide to a primary alcohol;
(3) halogenating the primary alcohol to give a halide;
(4) cyclizing the halide with sodium hydride to produce a chiral 2-piperidinone; and
(5) acylating an alpha carbon of the 2-piperidinone to give a chiral trans-3,4-disubstituted 2-piperidinone.

9. A method according to claim 8, wherein the chiral amine is a chiral primary amine or chiral amino acid derivative.
10. A method according to claim 8, wherein the aromatic group of the chiral amine is phenyl.
11. A method according to claim 8, wherein the alkyl group of the chiral amine is methyl.
12. A method according to claim 8, wherein the chiral amine is methyl benzylamine.
13. A method according to claim 8, wherein the chiral amine is (S)-methylbenzylamine.
14. A method according to claim 8, wherein $R^1$ is 4-F-$C_6H_4$.
15. A method for the preparation of a trans-3,4-disubstituted piperidine of the formula of

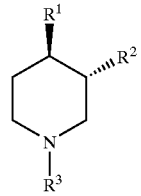

wherein $R^1$ is aryl, or 4-fluorophenyl, $R^2$ is alkyl, or any group substituted alkyl, and $R^3$ is aryl substituted alkyl, comprising:
(1) reacting a 3-substituted glutaric anhydride of the formula

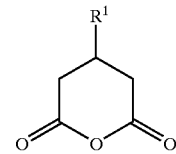

wherein $R^1$ is aryl, or 4-fluorophenyl with a chiral amine of the formula (I)

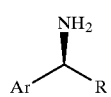

as a chiral auxiliary to obtain a mixture of hemiamides, wherein Ar represents an aromatic group and R represents an alkyl group;

(2) reducing an acid group of the hemiamide to a primary alcohol;

(3) halogenating the primary alcohol to give a halide;

(4) cyclizing the halide with sodium hydride to produce a chiral 2-piperidinone;

(5) acylating at the alpha carbon of the 2-piperidinone to give a chiral trans-3,4-disubstituted 2-piperidinone; and (6) reducing ester and amide groups of the chiral 3,4-disubstituted 2-piperidinone to form a trans-3,4-disubstituted piperidine.

16. A method for the preparation of a chiral paroxetine comprising:

(1) reacting a 3-aryl glutaric anhydride of the formula

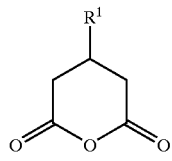

wherein $R^1$ is 4-fluorophenyl with a chiral amine of the formula (I)

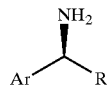

as a chiral auxiliary to obtain a mixture of hemiamides, wherein Ar represents an aromatic group and R represents an alkyl group;

(2) reducing an acid group of the hemiamide to a primary alcohol;

(3) halogenating the primary alcohol to give a halide;

(4) cyclizing the halide with sodium hydride to produce a chiral 2-piperidinone;

(5) acylating at the alpha carbon of the 2-piperidinone to give a chiral trans-3,4-disubstituted 2-piperidinone;

(6) reducing ester and amide groups of the chiral trans-3,4-disubstituted 2-piperidinone to provide a trans-3,4-disubstituted piperidine; and, (7) converting a hydroxyl group of trans-3,4-disubstituted piperidine to an aryl ether and then removing the chiral auxiliary by hydrofenolysis to obtain a chiral paroxetine hydrochloride.

17. A method for the preparation of a chiral paroxetine comprising:

(1) reacting a 3-aryl glutaric anhydride of the formula

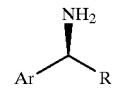

wherein $R^1$ is 4-fluorophenyl with a chiral amine of the formula (I)

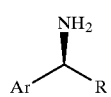

as a chiral auxiliary to obtain a mixture of hemiamides, wherein Ar represents aromatic groups and R represents alkyl groups;

(2) reducing an acid group of the hemiamide to a primary alcohol;

(3) halogenating the primary alcohol to give a halide;

(4) cyclizing the halide with sodium hydride to produce a chiral 2-piperidinone;

(5) acylating at the alpha carbon of the 2-piperidinone to give a chiral trans-3,4-disubstituted 2-piperidinone;

(6) reducing ester and amide groups of the chiral trans-3,4-disubstituted 2-piperidinone to provide a trans-3,4-disubstituted piperidine;

(7) crystallizing the trans-3,4-disubstituted piperidine and converting a hydroxyl group of this compound to a sulfonate followed by a treatment with sesamol and potassium alkoxide to provide a free amine;

(8) converting the free amine to a hydrochloride salt and purifying the hydrochloride salt by recrystallization; and (9) removing the chiral auxiliary by hydrogenolysis to obtain a chiral paroxetine hydrochloride.

18. (3S)-3-(4-fluorophenyl)-5-oxo-5-(1S)-(1-phenylethylamino) pentanoic acid of the following formula

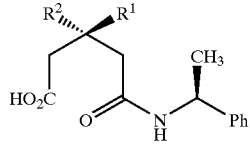

wherein $R^1$ represents 4-F—$C_6H_4$ and $R^2$ represents H.

19. (3S)-3-(4-fluorophenyl)-5-oxo-5-(1S)-(1-phenylethylamino) pentanoic acid of the following formula

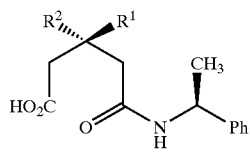

wherein $R^1$ represents H and $R^2$ represents 4-F—$C_6H_4$.

20. (3R)-3-(4-fluorophenyl)-5-hydroxypentanoic acid (1S)-1-phenylethylamide.

21. (3S)-5-bromo-3-(4-fluorophenyl) pentanoic acid (1S)-1-phenylethyl amide.

* * * * *